(12) United States Patent
Saruwatari

(10) Patent No.: US 6,608,234 B2
(45) Date of Patent: Aug. 19, 2003

(54) PROCESS FOR PRODUCING BISPHENOL A

(75) Inventor: Tetsuya Saruwatari, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/204,004

(22) PCT Filed: Nov. 30, 2001

(86) PCT No.: PCT/JP01/10510
§ 371 (c)(1),
(2), (4) Date: Aug. 16, 2002

(87) PCT Pub. No.: WO02/053521
PCT Pub. Date: Jul. 11, 2002

(65) Prior Publication Data
US 2003/0013926 A1 Jan. 16, 2003

(30) Foreign Application Priority Data
Dec. 28, 2000 (JP) ........................................ 2000/399933

(51) Int. Cl.⁷ .............................................. C07C 39/16
(52) U.S. Cl. ...................................................... 568/728
(58) Field of Search .......................................... 568/728

(56) References Cited

U.S. PATENT DOCUMENTS 6,414,199 B1   7/2002   Saruwatari
6,486,363 B1 * 11/2002   Berg

FOREIGN PATENT DOCUMENTS

| EP | 342758 | 11/1989 |
| EP | 754666 | 1/1997 |
| JP | 11-246458 | 9/1999 |

* cited by examiner

Primary Examiner—Michael L. Shippen
(74) Attorney, Agent, or Firm—Oblon, Spivak, McClelland, Maier & Neustadt, P.C.

(57) ABSTRACT

There is disclosed a method of producing bisphenol A, in which bisphenol A is produced by condensation of phenol and acetone with the use of a cation exchange resin as a catalyst and a free mercaptan as a promoter, comprising feeding phenol and acetone to a multi-stage reactor in which at least two fixed bed-type adiabatic reactors packed with the cation exchange resin are arranged in series and a heat exchanger is provided at an inlet of each of the reactors, and controlling the temperature within each of the reactors so as not to exceed 90° C.

With this method, elimination of sulfonic groups from the cation exchange resin as a catalyst can be suppressed, so that bisphenol A of high quality can be obtained, and the amount of the catalyst used can be reduced.

7 Claims, No Drawings

PROCESS FOR PRODUCING BISPHENOL A

TECHNICAL FIELD

The present invention relates to a method of producing bisphenol A [2,2-bis (4-hydroxyphenyl) propane]. More specifically, the present invention relates to an industrially useful method of producing bisphenol A in which, in the production of bisphenol A from phenol and acetone with the use of a cation exchange resin as a catalyst and a free mercaptan as a promoter, a multi-stage reactor is employed, whereby elimination of sulfonic groups from the cation exchange resin can be suppressed, so that bisphenol A of high quality can be obtained, and the amount of the catalyst used can be reduced.

BACKGROUND OF THE INVENTION

Bisphenol A has been known as an important compound for raw material for engineering plastics, such as polycarbonate resins, polyacrylate resins, etc, or for epoxy resins, and the demand for it tends to be still more growing recently.

Bisphenol A is produced by the condensation of an excess of phenol and acetone in the presence of an acid catalyst and optionally a promoter, such as a sulfur compound, etc.

As the acid catalyst for that reaction, inorganic mineral acids, such as sulfuric acid, hydrochloric acid, etc. were conventionally used. However, cation exchange resins have recently attracted attention (GB Patent Nos. 842209, 849565 and 883391), and have come to be industrially used.

On the other hand, it has been known that as for sulfur compounds used as the promoter, alkyl mercaptans with or without substituting groups, such as methyl mercaptan, ethyl mercaptan, thioglycolic acid, etc., are useful (U.S. Pat. Nos. 2,359,242 and 2,775,620). The mercaptans function to increase the reaction rate and improve the selectivity. For example, as reaction by-products in the production of bisphenol A, 2-(2-hydroxyphenyl)-2-(4-hydroxyphenyl) propane (a combination of o- and p'-types) is mainly formed, and tris-phenol, polyphenol, etc. are also formed. Especially, in cases where bisphenol A is used as raw material for polycarbonate resins, polyacrylate resins, etc., required is colorless high purity bisphenol A containing a reduced amount of those by-products. To this end, mercaptans are used as a promoter in order not only to increase the reaction rate but also to suppress the formation of the by-products and increase the selectivity.

With respect to the reaction temperature at which phenol and acetone are condensed to produce bisphenol A, disclosed are, for example, (1) the method in which phenol and acetone are subjected to a catalytic reaction with the addition of ethyl mercaptan at a reaction temperature of 60–85° C. (Japanese Patent Publication No. 52(1977)-12700), (2) the method in which phenol and acetone are reacted at a molar ratio of phenol/acetone of 2–10 in the presence of a strong acid at a temperature not exceeding 80° C. (Japanese Patent Publication No. 52(1977)-42790), (3) the method in which acetone is substantially completely reacted in the presence of an acidic chemical agent at a temperature not exceeding 80° C. (Japanese Patent Publication No. 57(1982)-14329).

However, in the above method (1), there is a prerequisite in that the reaction is carried out in one step, and it is required that the degree of conversion be made low or the temperature at the inlet be made low and the amount of the catalyst be made large when a adiabatic reactor with a fixed bed is used under such prerequisite at temperatures not greater than 85° C. Thus, the above method (1) is not efficient. On the other hand, in both the above methods (2) and (3), there is a prerequisite in that hydrochloric acid or sulfuric acid is used as the catalyst, and cation exchange resins are not used.

DISCLOSURE OF THE INVENTION

An object of the present invention is to provide an industrially useful method of producing bisphenol A in which, in the production of bisphenol A from phenol and acetone with the use of a cation exchange resin as a catalyst and a mercaptan as a promoter, a multi-stage reactor is employed, whereby elimination of sulfonic groups from the cation exchange resin can be suppressed, so that bisphenol A of high quality can be obtained, and the amount of the catalyst used can be reduced.

The inventors of the present invention have found, through extensive studies to achieve the above-mentioned object, that the above-mentioned object can be achieved by arranging at least two fixed bed-type adiabatic reactors in series and controlling the temperature of each of the reactors at less than 90° C. The present invention has been made based on the above finding.

Specifically, the present invention provides a method, in which bisphenol A is produced by condensation of phenol and acetone with the use of a cation exchange resin as a catalyst and a free mercaptan as a promoter, comprising feeding phenol and acetone to a multi-stage reactor in which at least two fixed bed-type adiabatic reactors packed with the cation exchange resin are arranged in series and a heat exchanger is provided at an inlet of each of the reactors, and condensing the phenol and acetone while the temperature within each of the reactors is controlled so as not to exceed 90° C.

BEST MODE FOR CARRYING OUT THE INVENTION

The method according to the present invention is a method of producing bisphenol A in which phenol and acetone are condensed with the use of a cation exchange resin as a catalyst and a free mercaptan as a promoter. There is no specific limitation with respect to the kind of the cation exchange resin to be used, and any of those which are conventionally employed as catalysts for the production of bisphenol A can be used. However, sulfonic acid type cation exchange resins are preferred especially in terms of the catalytic activity.

There is no specific limitation with respect to the kind of the sulfonic acid type cation exchange resins to be used inasmuch as they are strong acidic cation exchange resins having sulfonic groups. Examples of the sulfonic acid type cation exchange resin include sulfonated styrene-divinyl benzene copolymer, sulfonated cross-linked styrene polymer, phenol formaldehyde-sulfonic acid resin, benzene formaldehyde-sulfonic acid resin, etc. These may be used singly or in combination.

On the other hand, the free mercaptan as the promoter as used herein means a compound having a free form of SH group in the molecule. As the free mercaptan, an alkyl mercaptan can be adopted, which may be either of a non-substituted alkyl mercaptan and a substituted alkyl mercaptan having at least one substituting group, such as a carboxylic group, an amino group, a hydroxyl group, etc. Examples of non-substituted alkyl mercaptan include methyl mercaptan, ethyl mercaptan, n-butyl mercaptan, n-octyl mercaptan, etc. Examples of the substituted alkyl mercaptan include mercaptocarboxylic acids such as thioglycolic acid, β-mercaptopropionic acid, etc., aminoalkane thiols, such as 2-amino ethane thiol, 2,2-dimethyl thiazolidine, etc., mercaptoalcohols, such as mercaptoethanol, etc. Among these, the non-substituted alkyl mercaptans are especially preferred in terms of the promoting action. In addition, these mercaptans may be used singly or in combination.

The amount of each of these mercaptans is generally selected to be in the range of 0.1–20 mole %, preferably in the range of 1–10 mole %, relative to acetone, which is one of the raw materials to be used.

Further, there is no specific limitation with respect to the ratio of the amount between phenol and acetone, but it is desirable that the amount of unreacted acetone is as small as possible in terms of the easiness of purification of the produced bisphenol A and from an economical point of view. Therefore, it is advantageous that phenol is employed in an amount in excess of its stoichiometric amount. Generally, phenol is employed in an amount of 3–30 moles, preferably 5–15 moles, per one mole of acetone.

Meanwhile, the method of producing bisphenol A according to the present invention does not generally require a reaction solvent except for the cases where the reaction is carried out at such low temperatures that the viscosity of the reaction liquid is too high or the reaction liquid solidifies resulting in difficulty in operation.

In the method according to the present invention, there is used a multi-stage reactor in which at least two fixed bed-type adiabatic reactors packed with the cation exchange resin are arranged in series and a heat exchanger is provided at an inlet of each of the reactors. Phenol and acetone are fed to the multi-stage reactor and a free mercaptan as a promoter is also fed to the multi-stage reactor. There is no specific limitation with respect to the way in which the above feeding is carried out. In this respect, phenol, acetone and a free mercaptan may be fed to the first stage reactor in a lump-sum manner. Alternatively, phenol may be fed to the first stage reactor only and acetone and a free mercaptan may be each fed to each reactor in a divided manner.

In the method according to the present invention, the reaction temperature is controlled with a heat exchanger provided at an inlet of each reactor so that the temperature inside each reactor does not exceed 90° C. If the reaction temperature exceeds 90° C., elimination of the sulfonic groups from the cation exchange resin occurs, resulting in deterioration of the quality of the product, bisphenol A. The reaction temperature preferably ranges from 40° C. to less than 90° C., and especially preferably ranges from 60° C. to less than 90° C. If the reaction temperature is less than 40° C., the reaction rate becomes low and the reaction viscosity becomes extremely high which may create a risk of solidification.

The molar ratio of acetone/phenol in this reaction is generally selected to be in the range of 1/30 to 1/3, and preferably in the range of 1/15 to 1/5. If this molar ratio is lower than 1/30, there is a risk that the reaction rate becomes too low. If the molar ratio is greater than 1/3, more impurities are generated and the selectivity of bisphenol A tends to be lower.

Meanwhile, the molar ratio of the free mercaptan/acetone is generally selected to be in the range of 0.1/100 to 20/100, and preferably in the range of 1/100 to 10/100. If this molar ratio is lower than 0.1/100, there is a risk that improvements with respect to the reaction rate and the selectivity of bisphenol A are not sufficiently obtained. If this molar ratio is greater than 20/100, advantages are not fully enjoyed relative to the amount of the free mercaptan used.

Further, LHSV (Liquid Hourly Space Velocity) is generally selected to be in the range of 0.2 hr$^{-1}$ to 30 hr$^{-1}$, and preferably in the range of 0.5 hr$^{-1}$ to 10 hr$^{-1}$, at the final stage reactor.

In the method according to the present invention, the reaction mixture coming from the multi-stage reactor is subjected to a post treatment in a conventional way, whereby bisphenol A is obtained.

Explaining an example of the post treatment, concentration is first carried out prior to crystallization. Although there is no specific limitation with respect to the conditions under which the concentration is carried out, the concentration is generally carried out under the conditions in which the temperature is in the range of 130° C. to 170° C. and the pressure is in the range of 13 kPa to 53 kPa. If the temperature is lower than 130° C., high vacuum is requires. If the temperature is higher than 170° C., more impurities are generated and coloring is caused thereby. Further, it is advantageous that the concentration of bisphenol A in the concentrated residue ranges from 25 wt. % to 40 wt. %. If this concentration is less than 25 wt. %, the yield of bisphenol A is low. If this concentration exceed 40 wt. %, it becomes difficult to carry the slurry after the crystallization.

Crystallization of an addition product composed of bisphenol A and phenol from the concentrated residue is generally carried out by means of the vacuum cooling crystallization method in which cooling is performed using evaporation latent heat of water under reduced pressure. In the vacuum cooling crystallization method, water is added to the concentrated residue in an amount of 3–20 wt. %, and the crystallization treatment is carried out generally at a temperature of 40–70° C. and a pressure of 3–13 kPa. If the amount of water added is less than 3 wt. %, heat removing capability is insufficient, and if this amount exceeds 20 wt. %, dissolution loss of bisphenol A becomes large, both of which cases are not desirable. Further, if the temperature of the crystallization treatment is lower than 40° C., there is a risk of increase in the viscosity after the crystallization and occurrence of solidification. If the temperature of the crystallization treatment exceeds 70° C., dissolution loss of bisphenol A becomes large. Both of these cases are not desirable.

Thereafter, the addition product composed of bisphenol A and phenol as thus obtained by way of the crystallization treatment is separated by a conventional method, and is then subjected to a washing treatment generally using phenol. After that, the washed addition product is subjected to a disassembly processing into bisphenol A and phenol. The temperature at which the disassembly processing is carried out is generally selected to be in the range of 130–200° C., and preferably in the range of 150–180° C. The pressure at which the disassembly processing is carried out is generally selected to be in the range of 3–20 kPa.

High quality bisphenol A can be obtained from the bisphenol A thus obtained from the disassembly processing through removing the residual phenol in the latter bisphenol A substantially completely by the steam striping method, etc.

EXAMPLES

The present invention will hereinbelow be described in further detail based on examples. However, the present invention is not limited to such examples in any way.

Example 1

Three adiabatic reactors were arranged in series, and a heat exchanger was provided at the inlet of each of the reactors. A cation exchange resin (sulfonated styrene-divinyl benzene copolymer available from Mitsubishi Chemical Corporation; Product Name: DIAION SK 104) was introduced into each of the reactors.

Phenol was fed to the first stage reactor only and acetone and ethyl mercaptan as a promoter were each fed to each of the three reactors in a divided manner.

The reaction was carried out under the conditions in which the molar ratio of the total acetone/phenol was set to be 1/6.5, the molar ratio of the total ethyl mercaptan/acetone was set to be 5/100, LHSV at the last stage reactor was set to be 1 $hr^{-1}$, and the temperature at the inlet of each reactor was set to be 79° C. In this case, the maximum temperature at the outlets of the reactors was 87° C.

The color of the dissolved state of product bisphenol A obtained from the reaction mixture through a common post treatment method was APHA 15.

Example 2

The reaction was carried out in the same manner as in Example 1 except that LHSV at the last stage reactor was changed to 0.9 $hr^{-1}$, and the temperature at the inlet of each reactor was changed to 70° C. In this case, the maximum temperature at the outlets of the reactors was 77° C.

The color of the dissolved state of product bisphenol A obtained from the reaction mixture through a common post treatment method was APHA 15.

Comparative Example 1

The reaction was carried out in the same manner as in Example 1 except that the temperature at the inlet of each reactor was changed to 83° C. In this case, the maximum temperature at the outlets of the reactors was 91° C.

The color of the dissolved state of product bisphenol A obtained from the reaction mixture through a common post treatment method was APHA 20.

INDUSTRIAL APPLICABILITY

According to the present invention, in the production of bisphenol A from phenol and acetone with the use of a cation exchange resin as a catalyst and a free mercaptan as a promoter, a multi-stage reactor is used, whereby elimination of sulfonic groups from the cation exchange resin is suppressed, so that bisphenol A of high quality can be obtained, and the amount of the catalyst used can be reduced.

What is claimed is:

1. A method of producing bisphenol A, in which bisphenol A is produced by condensation of phenol and acetone with the use of a cation exchange resin as a catalyst and a free mercaptan as a promoter, comprising feeding phenol and acetone to a multi-stage reactor in which at least two fixed bed-type adiabatic reactors packed with the cation exchange resin are arranged in series and a heat exchanger is provided at an inlet of each of the reactors, and condensing the phenol and acetone while the temperature within each of the reactors is controlled so as not to exceed 90° C.

2. A method of producing bisphenol A according to claim 1, wherein the cation exchange resin is a sulfonic acid type cation exchange resin.

3. A method of producing bisphenol A according to claim 1, wherein the free mercaptan is an alkyl mercaptan, mercaptocarboxylic acid, aminoalkane thiol or mercaptoalcohol.

4. A method of producing bisphenol A according to claim 1, wherein the molar ratio of acetone/phenol is in the range of 1/30–1/3.

5. A method of producing bisphenol A according to claim 1, wherein the molar ratio of the free mercaptan/acetone is in the range of 0.1/100–20/100.

6. A method of producing bisphenol A according to claim 1, wherein the condensation is carried out while the temperature within each reactor is controlled to be between 40° C. and less than 90° C.

7. A method of producing bisphenol A according to claim 1, wherein LHSV at a final stage reactor is in the range of 0.2–30 $hr^{-1}$.

* * * * *